US008569011B2

(12) United States Patent
Annereau et al.

(10) Patent No.: US 8,569,011 B2
(45) Date of Patent: Oct. 29, 2013

(54) FLUORESCENT DERIVATIVES OF POLYAMINES, METHOD FOR PREPARING SAME AND APPLICATIONS THEREOF AS DIAGNOSIS TOOLS IN THE TREATMENT OF CANCEROUS TUMORS

(75) Inventors: Jean-Philippe Annereau, Toulouse (FR); Jean-Marc Barret, Castres (FR); Yves Guminski, Lagarrigue (FR); Thierry Imbert, Viviers les Montagnes (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 13/493,556

(22) Filed: Jun. 11, 2012

(65) Prior Publication Data
US 2012/0252059 A1    Oct. 4, 2012

Related U.S. Application Data (62) Division of application No. 12/670,611, filed as application No. PCT/EP2008/059890 on Jul. 28, 2008, now abandoned.

(30) Foreign Application Priority Data

Jul. 26, 2007   (FR) ...................................... 07 56743

(51) Int. Cl.
G01N 21/64        (2006.01)
(52) U.S. Cl.
USPC .......................................................... 435/34
(58) Field of Classification Search
USPC .......................................................... 435/34
See application file for complete search history.

(56) References Cited

U.S. PATENT DOCUMENTS 5,468,854 A    11/1995  McCabe et al.
6,172,261 B1*   1/2001  Vermeulin et al. ............... 506/15
7,846,926 B2* 12/2010  Imbert et al. ............... 514/232.8

FOREIGN PATENT DOCUMENTS

WO   WO 2004/093874 A1   11/2004
WO   WO 2005/100363 A1   10/2005

OTHER PUBLICATIONS

Ware et al. Langmuir 1988, vol. 4, p. 458-463.*
Blagsbrough, "Practical Synthesis of Unsymmetrical Polyamine Amides", Tetrahedron Letters, vol. 39 (1998) pp. 439-442.
Ducker et al., "In vitro and cellular assays for palmitoyl acyltransferases using fluorescent lipidated peptides", Methods, vol. 40 (2006) pp. 166-170.
Felschow et al., "Selective labeling of cell-surface polyamine-binding proteins on leukaemic and solid-tumour cell types using a new polyamine photoprobe", Biochemistry, vol. 328 (1997) pp. 889-895.
French Preliminary Search Report issued in French Application No. 0756743 on Apr. 10, 2008.
Ghosh et al., Potential Antileukemic and Immunosuppressive Drugs. Prepartion and in Vitro Pharmacological Acticity of Some Benzo-2, 1,3-oxadiazoles (Benezofurazans) and Their N-Oxides (Benzofuroxans). Journal of the Medicinal Chemistry. vol. 11, No. 2 (1968) pp. 305-311.
Guminski et al., "Synthesis of conjugated spermine derivatives with 7-nitrobenzoxadiazole (NBD), rhodamine and bodipy as new fluorescent probes for the polyamine transport system", Bioorganic & Medicinal Chemistry Letters, vol. 19 (2009) pp. 2474-2477.
Hadrich et al., "Synthesis and Characterization of Fluorescent Ligands for the Noreprinephrine Transporter: Potential Neuroblastoma Imaging Agents", J. Med. Chem., vol. 42 (1999) pp. 3101-3108.
Heberer et al., "Derivatisierung von Aminen mit 4-substituierten 7-Nitrobenz-2,1,3-oxadiazolen", Journal Fur Praktische Chemie, vol. 327, No. 3 (1985) pp. 487-504.
International Search Report issued in International Application No. PCT/EP2008/059890 on Oct. 8, 2008.
Lee et al., "Synthesis and Evaluation of Taxol-Folic Acid Conjugates as Targeted Antineoplastics", Bioorganic & Medicinal Chemistry, vol. 10 (2002) pp. 2397-2414.
Li et al., "Synthesis and Pharmaceological Activity of Fluorescent Histamine H2 Receptor Antagonists Related to Potentidine", Bioorganic & Medicinal Chemistry Letters, vol. 12 (2003) pp. 1717-1720.
Min et al., "Novel fluorescent asparaginyl-N-acetyl-D-glucosamines (Asn-GlcNAc) for the resolution of oligosaccharides in glycopeptides, based on enzyme transglycosylation reaction", Analytica Chimica Acta. vol. 550 (2005) pp. 173-181.
Ohba et al., "Synthesis of N-functionalized oleamide derivatives", Tetrahedron, vol. 63 (2007) pp. 3754-3761.
Onoda et al., "A Photoinduced Electron-Transfer Reagent for Peroxyacetic Acid, 4-Ethylthioacetylamino-7-phenylsultonyl-2, 1, 3-benzoxadiazole. Based on the Method for Predicting the Fluorescence Quantum Yields", Anal. Chem., vol. 74 (2002) pp. 4089-4096.
Onoda et al., The effects of spacer length on the fluorescence quantum yields of the benzofurazan compounds bearing a donor-acceptor system, Luminescence, vol. 17 (2002) pp. 11-14. XP002470773.

(Continued)

Primary Examiner — Yong Chu
(74) Attorney, Agent, or Firm — Birch, Stewart, Kolasch & Birch, LLP.

(57) ABSTRACT

The invention relates to novel fluorescent derivatives of polyamines having a benzoxadiazole group, to a method for preparing the same and to the use thereof as diagnosis tools for emphasising the polyamine transport system in cancerous cells in order to adapt the treatment thereof, and thus for selecting patients carrying such tumors in order to adapt their treatment. The derivatives are of the formula (I) or a pharmaceutically acceptable salt thereof, in which: $R_1$ is one or more $NO_2$ groups in position 4 or 6, or a $SO_2Ph$, $SO_2NMe_2$, $SO_2NH_2$ or $SO_3H$ group; $R_2$ is hydrogen, $C_{1-6}$ alkyl, benzyl, a perfluoroalkyl group; the values of a, b, c range from 2 to 5 independently from each other and represent alkylene chains separating the amino groups, and the values of d and e can independently be 0 or 1.

12 Claims, 1 Drawing Sheet (56) References Cited

OTHER PUBLICATIONS

Prados et al., "4-N, N-Dimethylaminosulfonyl-7-N-(2-aminoethyl)aminobenzofurazan as a new precolumn fluorescence derivatization reagent for carboxylic acids (fatty acids and drugs containing a carboxyl moiety) in liquid chromatography", Analytica Chimica Acta, vol. 344 (1997) pp. 227-232.

Robson et al., "Chemical Synthesis and Biological Properties of Novel Fluorescent Antifolates in Pgp- and MRP-Overexpressing Tumour Cell Lines", Biochemical Pharmacology, vol. 56 (1998) pp. 807-816.

Taliani et al., "New Fluorescent 2-Phenylindolglyoxylamide Derivatives as Probes Targeting the Peripheral-Type Benzodiazepine Receptor: Design, Synthesis, and Biological Evaluation", J. Med. Chem., vol. 50 (2007) pp. 404-407.

Toyo'oka et al., "4-(Aminosulfonyl)-2, 1, 3-benzoxadiazole derivatives as precolumn fluorogenic tagging reagents for carboxylic acids in high-performance liquid chromatography", Chemical Abstracts Service, Columbus, Ohio (1991) XP-002470774.

Toyo'oka et al., "Novel fluorescent chelating agent, and method for measuring metal ion", Chemical Abstracts Serivce, Columbus, Ohio (2004) XP00240772.

Toyo'oka et al., "Precolumn fluorescence tagging reagent for carboxylic acids in high-performance liquid chromatography: 4-substituted-7-aminoalkylamino-2, 1,3-benzoxadiazoles", Journal of Chromatography, vol. 588 (1991) pp. 61-71.

Toyo'oka et al., "Reaction of Amines of Biological Importance with 4-Fluoro-7-Nitrobenzo-2-oxa-1, 3-Diazole", Analytica Chimica Acta, vol. 149 (1983) pp. 305-312.

Uchiyama et al., "Effects of the substituent groups at the 4- and 7-positions on the fluorescence characteristics of benzofurazan compounds", J. Chem. Soc. Perkin Trans., vol. 2 (1998) 2165-2173.

Uchiyama et al., "Semi-empirical PM3 calculation reveals the relationship between the fluorescence characteristics of 4,7-disubstituted benzofurazan compounds, the LUMO energy and the dipole moment directed from the 4- to the 7-position", J. Chem. Soc., Perkin Trans, vol. 2 (1999) pp. 569-576.

Villa et al., "Choline and phosphatidylcholine fluorescent derivatives localization in carcinoma cells studied by laser scanning confocal fluorescence microscopy". European Journal of Cancer, vol. 41 (2005) pp. 1453-1459.

Ware et al., "Interaction of a Fluorescent Spermine Derivative with a Nucleic Acid Polyion", Langmuir, vol. 4 (1988) pp. 458-463.

* cited by examiner

Cells A549 (non-small cell lung cancer)

FIG 1.A.

Cells MRC5 (healthy lung)

FIG 1.B.

FIGURE 1

FLUORESCENT DERIVATIVES OF POLYAMINES, METHOD FOR PREPARING SAME AND APPLICATIONS THEREOF AS DIAGNOSIS TOOLS IN THE TREATMENT OF CANCEROUS TUMORS

NOVEL FLUORESCENT DERIVATIVES OF POLYAMINES, METHOD FOR PREPARING SAME AND APPLICATIONS THEREOF AS DIAGNOSIS TOOLS IN THE TREATMENT OF CANCEROUS TUMORS

CROSS REFERENCE TO RELATED APPLICATIONS:

This application is a Divisional of Application No. 12/670,611 filed on Jan. 25, 2010 now abandoned, which is a National Phase of PCT International Application No. PCT/EP2008/059890 filed on Jul. 28, 2008, which claims the benefit of patent application Ser. No. 0,756,743 filed in France, on Jul. 26, 2007. The entire contents of all of the above applications is hereby incorporated by reference.

The marking of biomolecules and the follow-up of biological phenomena require the designing of fluorescent probes which have become indispensable tools for structural and functional studies of biological media.

A fluorescent probe is a conjugated molecule, consisting of a fluorophore or fluorochrome group linked covalently to a group having specific interaction properties with an adequate biological environment.

This fluorescent probe has the property of absorbing the light energy received at a well-defined, wavelength, thereby forming the excitation phase, then of restoring this energy in the form of fluorescent light called the emission phase. Therefore, after excitation, once the energy of the photon has been absorbed, the molecule lies in an electronically excited state and then returns to the state of fundamental energy by emitting a photon. This photon emission, a fluorescence phenomenon, occurs at a wavelength that is slightly greater than the excitation wavelength. A fluorescence spectrum can then be recorded which is specific to the molecule.

It is then possible to locate a fluorescent probe in a biological medium using fluorescence microscopes or a flow cytometer by exciting the preparation at as suitable wavelength.

There is a wide choice of fluorochromes such as the derivatives of fluorescein or rhodamine. Not all of them are suitable for biological follow-up. The essential characteristics are: the values of the excitation and emission wavelengths for feasibility of the study, an extinction coefficient adapted to the concentration of the probe used for the study, the quantum yield which allows a significant signal to be obtained with no energy loss and which is stable over time i.e. having a fairly long half-life in the excited state.

In addition, it is desirable for the chosen fluorophore to take part in the least manner possible in chemical reactions within its environment during measurement, otherwise this would lead to loss of its fluorescence properties i.e. signal loss.

Derivatives which have a benzoxadiazole backbone, also called benzofurazanes, have the required fluorescence properties. The values of the wavelengths used for excitation and emission, and the quality of the phenomenon in intensity and stability, are related to the structure of the compound and of its substituents.

These derivatives are known, fluorescence studies in relation to their substituents and their preparation are described (*J. Chem. Soc. Perkin Trans* 2, 1998, 2165, *J. Chem. Soc, Perkin Trans* 2, 1999, 569).

Benzoxadiazole fluorescent derivatives for biological use have been studied (*Anal. Chim. Acta*, 2005, 550, 173, *Bioorg. Med. Chem. Lett.* 2003, 13, 1717, *Luminscence*, 2002, 17, J. Med. Chem. 1999, 42, 3101).

Cancer remains one of the major causes of mortality in the Western world. The means to fight cancer i.e. prevention, surgery, radiotherapy, immunotherapy and chemotherapy still do not allow the disease to be eradicated in numerous cases.

The reasons for this failure partly lie in the difficulty to identify the tumor cell and to treat it selectively without causing too much damage to healthy tissue.

Benzoxadiazole—polyamine conjugated hybrid molecules can bring an answer to this problem.

For its proliferation, a cancerous cell requires a large number of essential biological elements, which include polyamines (spermine, spermidine, putrescine). Polyamines are indispensable for any cell in proliferation. Under normal conditions, endogenous synthesis of polyamine is sufficient for the cell, but with cancer cells an exogenous polyamine contribution is most often necessary by means of an active transport. The detection of this active transport allows detection of cancer cells and the follow-up of their progression in terms of growth and dissemination. However, at the present time, the transporter of polyamine in human cells has not been identified at molecular level. The only method to demonstrate its presence is therefore to use a probe recognized by this transporter which, by accumulating within the cell, gives information on the activity of the transporter.

The polyamine transporter is a protein complex whose structure is not known in detail.

This transporter plays an important role in the intracellular importing of natural polyamines i.e. putrescine, spermidine, and spermine.

These polyamines are essential for cell growth and development. Intracellular metabolism normally provides the needs of a healthy cell. This metabolism provides these polyamines from the cell's amino acids. Arginine converts to ornithine, ornithine undergoes decarboxylation to provide putrescine. This putrescine (C4) can be extended by a C3 chain by means of an adenosine methionine, followed by decarboxylation, to provide spermidine. The latter can again be extended by a C3 chain also by means of another methionine residue, to provide spermine.

These polyamines can also be broken down by oxidation with polyamineoxidases, and thereby convert back to spermidine and putrescine.

If the intracellular mechanism is disturbed (e.g. cancerous cell), the intracellular metabolism can no longer meet the cell's needs, and it will therefore procure polyamines from outside the cell.

This is where the polyamine transporter comes to be involved. It acts as feeder and regulator.

For example, in the case of the compound in example 27 of patent application WO 2005/100363: the <<epipodophyllotoxin>> structural moiety grafted on the spermine does not appear to modify recognition of the polyamine transporter, enabling the compound to be internalised in the tumor cell, which will subsequently play its part as cytotoxic agent. Similarly, fluorescent probes having a polyamine moiety will be recognized by the polyamine transporter.

Amongst the panel of cell lines studied in cancerology, there is variability in the expression of the polyamine transporter. Using diagnostic probes it is possible to determine previously (before anti-tumor treatment) which cells will be sensitive to treatment and those which will not be sensitive.

The greater intracellular fluorescence, the more the cell under consideration will be sensitive to treatment with a targeted anticancer agent (e.g. the compound in example 27 of patent application WO 2005/100363).

The present invention therefore relates to compounds consisting of a polyamine moiety bonded to a substituted benzoxadiazole moiety carrying fluorescence, which can be used as said probes. The polyamine part of these molecules will effectively be recognized by the polyamine transport system and the molecule will be internalised inside the cancer cell, whilst the moiety carrying fluorescence will be detected by conventional analysis systems in a biological medium, thereby allowing to select tumors which express the polyamine transport system.

The detection of this polyamine transport system on the cells therefore allows to select tumor-carrying patients who are able to be treated by an anti-cancer compound vectored by the polyamine transport system, irrespective of its mechanism of action.

Therefore, in tumors taken by biopsy or in leukaemia cells taken by puncture from hospitalised patients it will be possible to detect fluorescence that is proportional to the expression of the polyamine transporter. Patients with these tumors can then be selected so that they can be treated preferably with the anticancer compounds vectored towards the polyamine transport system, being assured of a much better chance of treatment response.

U.S. Pat. No. 6,172,261 and *Anal. Chim. Acta,* 1983, 149, 305 describe polyamines bonded to fluorophore groups. More particularly, B. R. Ware, in Langmuir (1988, 4, 458) describes a spermine derivative with a benzoxadiazole group, whose formula is given below, and its use as fluorescent polyamine derivative in the study on its interaction with oligonucleotides.

F 16746

Similarly, Ohba in (Tetrahedron, 2007, 63, 37-54) describes a derivative of putrescine with a benzoxadiazole group, whose formula is given below:

However, none of these publications mentions the use of derivatives of polyamine-benzoxadiazole to evidence tumor cells expressing the polyamine transport system.

The present invention concerns novel fluorescent derivatives consisting of a polyamine moiety on which a fluorescence-carrying moiety is bonded, i.e. substituted benzoxadiazole, their method of preparation and their use in detection of the polyamine transport system inside cells. It also concerns their use in selecting tumors expressing the polyamine transport system and their use in selecting patients carrying said tumors.

These derivatives correspond to following formula 1:

Formula 1 or a pharmaceutically acceptable salt thereof, in which:

$R_1$ represents one or two $NO_2$ groups at position 4 and/or 6, or a $SO_2Ph$, $SO_2NMe_2$, $SO_2NH_2$, $SO_2H$ group;

the polyamine chain can be at position 5, 6 or 7;

$R_2$ is a hydrogen, a $C_{1-6}$ alkyl, a benzyl, perfluoroalkyl group;

the values of a, b, c can be 2 to 5, independently of each other, and represent alkylene chains separating the amino groups;

the values d and e can be 0 or 1 independently, but cannot represent value 0 at the same time;

provided that when e=0, then R2 cannot be a hydrogen; and with the exception of the compound for which $R_1$=4-$NO_2$, $R_2$=H, a=3, b=4, c=3 and d=e=1.

The compounds of the present invention can be in the form of mineral or organic addition salts.

In the present invention, by <<pharmaceutically acceptable>> is meant which can be used to prepare a pharmaceutical composition which is generally safe, non-toxic and not biologically or otherwise undesirable, and which is acceptable for veterinary use and for human pharmaceutical use.

By <<pharmaceutically acceptable salt>> of a compound under the present invention is meant salts which are pharmaceutically acceptable such as defined herein and which have the desired pharmacological activity of the parent compound.

By <<addition salt>>, in the meaning of the present invention, is particularly meant an addition salt of a mineral or organic acid.

By way of example, mention can be made of acid addition salts formed with mineral acids such as hydrochloric acid, hydrobromic acid, sulfuric acid, nitric acid, phosphoric acid and similar; or formed with organic acids such as acetic acid, benzenesulfonic acid, benzoic acid, camphorsulfonic acid, citric acid, ethane-sulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, mandelic acid, methanesulfonic acid, muconic acid, 2-naphtalenesulfonic acid, propionic acid, salicylic acid, succinic acid, dibenzoyl-L-tartaric acid, tartaric acid, p-toluenesulfonic acid, trimethylacetic acid, trifluoroacetic acid and similar.

By <<4-$NO_2$>> under the present invention is meant a $NO_2$ (nitro) group at position 4.

By <<alkyl>> under the present invention is meant a saturated, straight or branched hydrocarbon chain, comprising 1 to 6 carbon atoms. In particular, it may be a methyl, ethyl, n-propyl, isopropyl, n-butyl, tert-butyl, isobutyl, pentyl or hexyl group.

By <<perfluoroalkyl>> under the present invention is meant an alkyl group such as defined above in which all the hydrogen atoms have been replaced by fluorine atoms.

Advantageously, $R_1$ represents one or two $NO_2$ groups at position 4 and/or 6, and more particularly a $NO_2$ group at position 4.

More particularly, the present invention concerns the compounds in which:
$R_1$=4-$NO_2$, $R_2$=$C_{1-6}$ alkyl, a=3, b=4, c=3, d=e=1,
$R_1$=4-$NO_2$, $R_2$=H or $C_{1-6}$ alkyl, a=0, b=4, c=3, d=0, e=1,
$R_1$=4-$NO_2$, $R_2$=H or $C_{1-5}$ alkyl, a=0, b=3, c=4, d=0, e=1, or
$R_1$=4-$NO_2$, $R_2$=$C_{1-6}$ alkyl, a=4, b=0, c=0, d=1, e=0.

Further particularly, the invention concerns the following compounds:

N-(3-Aminopropyl)-N'-{3-[methyl-(7-nitrobenzo[1,2,5]oxadiazol-4-yl)-amino]-propyl}-butane-1,4-diamine corresponding to the compound of formula 1 in which $R_1$=4-$NO_2$, $R_2$=Methyl, a=3, b=4, c=3, d=e=1, N-(3-Aminopropyl)-N'-methyl-N'-(7-nitrobenzo[1,2,5]oxadiazol-4-yl)-butane-1,4-diamine corresponding to the compound of formula 1 in which
$R_1$=4-$NO_2$, $R_2$=Methyl, a=0, b=4, c=3, d=0, e=1, N-(3-Aminopropyl)-N'-(7-nitrobenzo[1,2,5]oxadiazol-4-yl)-butane-1,4-diamine corresponding to the compound of formula 1 in which $R_1$=4-$NO_2$
$R_2$=H, a=0, b=4, c=3, d=0, e=1,

N*1*-{3-[methyl-(7-nitrobenzo[1,2,5]oxadiazol-4-yl)-amino]-propyl}-butane-1,4-diamine corresponding to the compound of formula 1 in which
$R_1$=4-$NO_2$, $R_2$=Methyl, a=0, b=3, c=4, d=0, e=1, N*1*-[3-(7-nitrobenzo[1,2,5]oxadiazol-4-yl-amino)-propyl]-butane-1,4-diamine corresponding to the compound of formula 1 in which $R_1$=4-$NO_2$,
$R_2$=H, a=0, b=3, c=4, d=0, e=1, and N*1*-Methyl-N*1*-(7-nitrobenzo[1,2,5]oxadiazol-4-yl)-butane-1,4-diamine corresponding to the compound of formula 1 in which $R_1$=4-$NO_2$,
$R_2$=Methyl, a=4, b=0, c=0, d=1, e=0.

The invention also concerns a method to synthesize the compounds of formula 1, characterized in that it comprises the following steps a), b) and c):

a) Coupling a derivative of benzoxadiazole of formula 2

Formula 2 in which $R_1$ represents one or two $NO_2$ groups at position 4 and/or 6, or a $SO_2Ph$, $SO_2NMe_2$, $SO_2NH_2$ or $SO_3H$ group; and advantageously a $NO_2$ group at position 4;

$R_3$ is a halogen substituent, mobile at ortho or para position of group $R_1$, with a polyamine of formula 6, at position 5, 6 or 7, i.e. at ortho or para position of group $R_1$, in which P is a protector group of the amine functions and in which a, b, c, d and e have the same meanings as those given previously.

Formula 6

The protector groups P can be BOC groups (tertiobutyloxycarbonyl) cleavable in acid medium (HCl or trifluoroacetic acid (TFA)) if the $R_1$ group=$NO_2$. If the benzoxadiazole has sulfonyl or sulfamido groups, then P can be a protector group of benzyloxycarbonyl type, cleavable by hydrogenolysis.

During this coupling reaction, the polyamine reacts with the benzoxadiazole by substitution of the halogen via treatment with a base in an inert solvent.

More particularly, the compound of formula 2 is 4-nitro-7-chlorobenzoxadiazole.

Further particularly, the inert solvent is acetonitrile and the base is Caesium carbonate.

The different benzoxadiazoles are described in the following publications: *J. Chem. Soc. Perkin Trans* 2, 1998, 2165, *J. Chem. Soc, Perkin Trans* 2, 1999, 569, Examples of polyamine derivatives, spermine derivatives protected by 3 benzyloxycarbonyl or tertiobutyloxycarbonyl groups are described in the publication: (*Tet. Let.* 1998, 39, 439).

b) The compound derived from the coupling reaction a) is alkylated by an alkyl halide in the presence of a base in an inert solvent. Preferably THF is used (tetrahydrofurane) as solvent.

Preferably, sodium hydride or an alkaline carbonate is used as base.

Also preferably, THF is used as solvent.

c) The compound derived from step b) is then deprotected in acid medium at ambient temperature to obtain the compounds of formula 1.

Preferably, this deprotection step is performed in hydrochloric acid or in trifluoroacetic acid.

The present invention also concerns the use of the compounds of following formula 1:

Formula 1 or a pharmaceutically acceptable salt thereof,
in which:
$R_1$ represents one or two $NO_2$ groups at position 4 and/or 6, or a $SO_2Ph$, $SO_2NMe_2$, $SO_2NH_2$ or $SO_3H$ group;
the polyamine chain can be at position 5, 6 or 7;
$R_2$ is a hydrogen, a $C_{1-6}$ alkyl, a benzyl, a perfluoroalkyl group;
the values of a, b, c can be 2 to 5, independently of each other, and represent alkylene chains separating the amino groups;
the values of d and e can be 0 or 1 independently, but cannot represent value 0 at the same time;
as fluorescent diagnostic probe to detect tumors expressing the polyamine transport system.

The compounds of the present invention can be in the form of mineral or organic addition salts.

Advantageously, $R_2$ is not a hydrogen when e=0.

Advantageously, $R_1$ represents one or two $NO_2$ groups at position 4 and/or 6, and more particularly a $NO_2$ group at position 4.

More particularly, the compounds of formula 1 which can be used as fluorescent diagnostic probe concern the compounds in which:

$R_1$=4-$NO_2$, $R_2$=$C_{1-6}$ alkyl, a=3, b 4, c=3, d=e=1,
$R_2$=4-$NO_2$, $R_2$=H or $C_{1-6}$ alkyl, a=0, b=4, c=3, d=0, e=1,
$R_1$=4-$NO_2$, $R_2$=H or $C_{1-6}$ alkyl, a=0, b=3, c=4, d=0, e=1, or
$R_1$=4-$NO_2$, $R_2$=$C_{1-6}$ alkyl, a=4, b=0, c=0, d=1, e=0.

Further particularly, the compounds of formula 1 concern the following compounds:

N-(3-Aminopropyl)-N'-{3-[methyl-(7-nitrobenzo[1,2,5]oxadiazol-4-yl)-amino]-propyl}-butane-1,4-diamine corresponding to the compound of formula 1 in which $R_1$=4-$NO_2$, $R_2$=methyl, a=3, b=4, c=3, d=e=1, N-(3-Aminopropyl)-N'-methyl-N'-(7-nitrobenzo[1,2,5]oxadiazol-4-yl)-butane-1,4-diamine corresponding to the compound of formula 1 in which
$R_1$=4-$NO_2$, $R_2$=Methyl, a=0, b=4, c=3, d=0, e=1, N-(3-Aminopropyl)-N'-(7-nitrobenzo[1,2,5]oxadiazol-4-yl)-butane-1,4-diamine corresponding to the compound of formula 1 in which $R_1$=4-$NO_2$
$R_2$=H, a=0, b=4, c=3, d=0, e=1, N*1*-{3-[methyl-(7-nitrobenzo[1,2,5]oxadiazol-4-yl)-amino]-propyl}-butane-1,4-diamine corresponding to the compound of formula 1 in which
$R_1$=4-$NO_2$, $R_2$=Methyl, a=0, b=3, c=4, d=0, e=1,

N*1*-[3-(7-nitrobenzo[1,2,5]oxadiazol-4-yl-amino)-propyl]-butane-1,4-diamine corresponding to the compound of formula 1 in which $R_1$=4-$NO_2$,
$R_2$=H, a=0, b=3, c=4, d=0, e=1, and N*1*-Methyl-N*1*-(7-nitrobenzo[1,2,5]oxadiazol-4-yl)-butane-1,4-diamine corresponding to the compound of formula 1 in which $R_1$=4-$NO_2$,
$R_2$=Methyl, a=4, b=0, c=0, d=1, e=0.

The following examples describe the different steps to prepare compounds of the invention, and are in no way limiting.

EXAMPLE 1

Synthesis of N-(3-aminopropyl)-N'-{3-(methyl-(7-nitrobenzo[1,2,5]oxadiazol-4-yl)-amino)-propyl}-butane-1,4-diamine The synthesis of the formula 1 compound is conducted following the scheme given below:

Scheme 1

3

4 formula 1

Stage 1: Preparation of triBOC spermine of formula 3 (*Bioorg. Med. Chem.* 2002, 10, 2397).

Formula 3

40 g of spermine are placed in solution in 300 mL of CH$_2$Cl$_2$, and cooled to 0° C. 23.8 mL of ethyl trifluoroacetate in solution in 50 mL of CH$_2$Cl$_2$ are added dropwise. The solution is left under stirring for 1 hour at room temperature. The residue obtained is dissolved in 600 mL THF, and 140.28 mL triethylamine are added. Next, solution of 174.48 g BOC$_2$O in 200 mL THF is added, maintaining the temperature at 20° C. Stirring at room temperature is continued for three hours, and the reaction medium is then poured onto water and extracted with isopropyl ether. After decanting, drying over sodium sulphate, filtration and evaporation, the organic solution is evaporated. The residue obtained is then dissolved in 900 mL of a MeOH/H$_2$O 8/2 mixture. 192.6 g of Caesium carbonate are added and the whole is left under reflux for three hours. After vacuum-evaporation of the methanol, water is added and extraction performed with isopropyl ether. The organic phase is decanted, and 0.5 N hydrochloric acid is added to this organic phase. It is allowed to settle. Three phases are seen to form. The middle phase in oil form contains the expected product in hydrochloride form. This phase is decanted, dissolved in CH$_2$Cl$_2$, and dried over sodium sulphate. After filtering and evaporation, 54 g of triBOC spermine hydrochloride are obtained in the form of a colourless oil which is used directly in the following step (Yield=50%). TLC SiO$_2$: CH$_2$Cl$_2$-MeOH—NH$_4$OH (90-10-10) Rf=0.5.

Stage 2: Condensation with the fluorophore.

5.39 g of the oil obtained at stage 1 are placed in solution in 100 mL acetonitrile, 6.42 g Caesium carbonate and 2 g of 4-chloro-7-nitrobenzo[1,2,5]oxadiazole under stirring. The mixture is refluxed for one hour. The reaction medium is fixed on silica and the solvent evaporated. The solid residue is placed at the top of a flash chromatography column and eluted with a gradient from pure heptane to the heptane-AcOEt mixture (50-50). This gives 4.4 g (66%) of red oil. TLC: S102 Heptane/AcOEt (50-50) Rf=0.3. APCI-MS m/z=666.3 (MH+); $^1$H NMR (CDCl$_3$): 8.47 (d, 1H, J=8 Hz, H$_5$), 7.96 (m, 1H, NH), 6.17 (d, 1H, J=8 Hz, H$_5$), 3.53 (m, 2H, NHCH$_2$), 3.38 (m, 2H, CH$_2$NH), 3.10-3.21 (m, 8H, NCH$_2$), 1.92 (m, 2H, CH$_2$), 1.66 (m, 2H, CH$_2$), 1.43-1.51 (m, 31H, CH$_2$, t-Bu).

Stage 3: R$_2$ alkylation. Preparation of the tertiobutylic ester of (3-{t-butoxycarbonyl-[4-(t-butoxycarbonyl-{3-[methyl-(7-nitrobenzo[1,2,5]oxadiazol-4-yl)-amino]-propyl}-amino)-butyl]-amino}-propyl)-carbamic acid of formula 5.

The compound obtained at the preceding stage (4.4 g) is dissolved in 150 mL acetonitrile, in the presence of 4 g Caesium carbonate and 2.05 mL methyl iodide. The reaction medium is stirred at ordinary temperature for four hours. The medium is fixed on silica by evaporation of the solvent, then chromatographed on a flash column of diameter 50 mm. With gradient elution from pure heptane to the heptane-AcOEt (50-50) mixture, 4.2 g of a red oil are obtained (Yield=93%). TLC: Heptane-AcOEt (30-70) Rf=0.4. ESI-MS m/z 680.4 (MH+); $^1$H NMR (DMSO): 8.48 (d, 1H, J=8 Hz, H$_5$), 6.40 (d, 1H, J=8 Hz, H$_6$), 3.47 (m, 2H, NHCH$_2$), 3.33 (s, 3H, NCH$_2$), 3.24 (m, 2H, CH$_2$NH), 3.15 (m, 2H, NCH$_2$), 3.08 (m, 4H, NCH$_2$), 2.88 (m, 2H, NCH$_2$), 1.91 (m, 2H, CH$_2$), 1.54 (m, 2H, CH$_2$), 1.36 (m, 31H, CH$_2$, t-Bu).

Stage 4: 4.2 g of the compound from the preceding stage are dissolved in 20 mL of a 4M HCl solution in dioxane and left under stirring for three hours at ordinary temperature. The orange precipitate of the hydrochloride is then filtered, rinsed with methanol then with ethyl ether. After vacuum drying, 2.8 g (92%) of the salt of N-(3-aminopropyl)-N'-{3-[(methyl-(7-nitrobenzo[1,2,5]oxadiazol-4-yl)-amino]-propyl}-butane-1,4-diamine, of formula 1 are obtained. F=260° C. ESI-MS m/z=380.2 (MH+); $^1$H NMR (D$_2$O): 8.50 (d, 1H, J=8 Hz, H$_5$), 6.41 (d, 1H, J=8 Hz, H$_6$), 4.27 (m, 2H, NHCH$_2$), 3.54 (s, 3H, NCH$_3$), 3.11-3.27 (m, 10H, CH$_2$NH), 2.26 (m, 2H, CH$_2$), 2.11 (m, 2H, CH$_2$), 1.82 (m, 4H, CH$_2$).

Similarly, the compounds of formula 1 in which d=0, e=1 and b=3, c=4 or else b=4 and c=3, can be prepared following the same methodology using di-protected spermine. The different methods used to prepare these protected polyamines of formula 6 (P=benzyloxycarbonyl or tertiobutyloxycarbonyl) are either described in patent application WO 2005/100363, or are indicated in the cited publications.

EXAMPLE 2

Synthesis of N-1-(7-Nitrobenzo[1,2,5]oxadiazol-4-yl]butane-1,4-diamine

This compound is described in the publication by Ohba et al: (Tet. 2007, 63, 3754).

It is synthesized according to the present invention by the following method:

Stage 1: In 5 mL acetonitrile, reflux for 30 minutes, a mixture consisting of 200 mg of 4-chloro-7-nitrobenzo[1,2,5]oxadiazole and of 190 mg of tertiobutyl ester of (4-aminobutyl)-carbamic acid, and of 320 mg of Caesium carbonate. After cooling, the medium is poured, onto water and extracted with ethyl acetate. It is decanted and the organic phase is dried over sodium sulphate. Filter and evaporate in vacuo. Flash chromatography on silica eluted with a gradient from pure heptane to pure ethyl acetate in 30 minutes allows the isolation of 280 mg (yield 80%) of the tertiobutyl ester of [4-(7-nitrobenzo[1,2,5]oxadiazol-4-ylamino)-butyl]-carbamic acid, in oil form. TLC SiO$_2$: Heptane-AcOEt (30-70), Rf=0.5. ESI-MS m/z=352.1 (MH+); $^1$H NMR (DMSO) 9.55 (s, 1H, NH), 8.50 (d, 1H, J=8 Hz, H$_5$), 6.83 (m, 1H, NH), 6.42 (d, 1H, J=8 Hz, H$_5$), 3.47 (m, 2H, NHCH$_2$), 2.96 (m, 2H, CH$_2$NH), 1.66 (m, 2H, CH$_2$), 1.48 (m, 2H, CH$_2$); 1.36 (s, 9H, t-Bu).

Stage 2: 280 mg of the carbamate obtained at the previous stage are placed in solution in 15 mL of methylene chloride and 2 mL of trifluoroacetic acid, then stirred for 15 minutes at room temperature. After evaporation, the oily residue obtained is crystallized in isopropyl ether. 150 mg (yield 51%) of N-1-(7-nitrobenzo[1,2,5]oxadiazol-4-yl]butane-1,4-diamine trifluoroacetate are isolated. TLC SiO$_2$: CH$_2$Cl$_2$-MeOH—NH$_4$OH (90/10/1), Rf=0.7. ESI-MS m/z=252.1 (MH$^+$); $^1$H NMR (DMSO) 9.54 (s, 1H, NH), 8.53 (d, 1H, J=8 Hz, H$_5$), 7.70 (s, 2H, NH$_2$), 6.44 (d, 1H, J=8 Hz, H$_5$), 3.50 (m, 2H, NHCH$_2$), 2.84 (m, 2H, CH$_2$NH), 1.59-1.76 (m, 4H, CH$_2$CH$_2$).

EXAMPLE 3

Synthesis of N-(3-Aminopropyl)-N'-[3-(7-methyl-benzo[1,2,5]oxadiazol-4-ylamino)-propyl]-butane-1-4-diamine Stage 1: 250 mg of triBOC spermine obtained at stage 1 in example 1 are left to react with 100 mg of dimethylamide of 4-fluorobenzo[1,2,5]oxadiazole-4-sulfonic acid in the presence of 0.17 mL of triethylamine in 10 mL of acetonitrile under stirring at ordinary temperature for 30 minutes. The reaction medium is poured onto water acidified with HCl and extracted with ethyl acetate. After decanting and washing the organic phase with NaCl-saturated water, the solution is dried over Na$_2$SO$_4$, filtered and evaporated. 250 mg of a yellow oil are obtained (Yd=84%). ESI-MS m/z=728.5 (MH+); $^1$H NMR (DMSO): 7.83 (d, 1H, J=8 Hz, H$_5$), 6.30 (d, 1H, J=8 Hz, H$_5$), 3.35 (m, 2H, NHCH$_2$), 2.68 (s, 6H, NMe$_2$), 3.23 (m, 2H, CH$_2$N), 3.14 (m, 6H, CH$_2$N), 2.87 (m, 2H, NCH$_2$), 1.86 (m, 2H, CH$_2$), 1.55 (m, 2H, CH$_2$), 1.36 (m, 31H, CH$_2$, t-Bu).

Stage 2: 250 mg of the protected compound previously obtained are stirred at room temperature for 30 minutes in 2 mL of trifluoroacetic acid and 10 mL of CH$_2$Cl$_2$. After evaporation, crystallization is performed with a quantitative yield of 260 mg of trifluoroacetate of N-(3-aminopropyl)-N'-(3-(7-methylbenzo[1,2,5]oxadiazol-4-ylamino)-propyl)-butane-1-4-diamine in isopropyl ether, with traces of acetone. ESI-MS m/z=428.3 (MH+); $^1$H NMR (DMSO): 7.84 (d, 1H, J=8 Hz, H$_5$), 6.37 (d, 1H, J=8 Hz, H$_6$), 2.85-3.05 (m, 12H, NHCH$_2$), 2.70 (s, 6H, NMe$_2$), 2.00 (m, 2H, CH$_2$), 1.90 (m, 2H, CH$_2$), 1.62 (s, 4H, CH$_2$).

EXAMPLE 4

Pharmacological Study

1. Selectivity of the Probes Vis-Á-Vis Tumor Cells.

Cells taken from biopsies are mechanically separated with or without the presence of trypsin depending on the constitution of the tissue under consideration. The haematopoietic cells are separated and isolated following conventional preparation methods for blood cells. Once isolated after a fairly short time to ensure the viability of the cells being examined, the cells are placed in the presence of the probe such as synthesized in examples 1 to 3 for example, and left to incubate in the recommended culture medium for the tissue under consideration in the presence of aminoguanidine. Aminoguanidine is used to prevent in vitro denaturating of the polyamines. No serum is used (too rich in polyamine and hence a source of measurement error). An incubation time of one to four hours is sufficient and allows detection of fluorescence by immunochemistry or flow cytometry, by choosing excitation and emission wavelengths compatible with the substituent of the fluorescent probe. This analysis is conducted by flow cytometry or histochemistry following standard methodology in the study described below, by exciting the probe obtained in example 1, N-(3-aminopropyl)-N'-{3-[methyl-(7-nitrobenzo[1,2,5]oxadiazol-4-yl)-amino]-propyl}-butane-1,4-diamine with a 488 nm source and measuring fluorescence emission at 525 nm. In this same example, A549 cells derived from a human lung cancer tumor (non-small cell) were assayed by comparison with MRC-5 cells derived from a healthy lung and commercially available from cell line banks.

Figure 1:
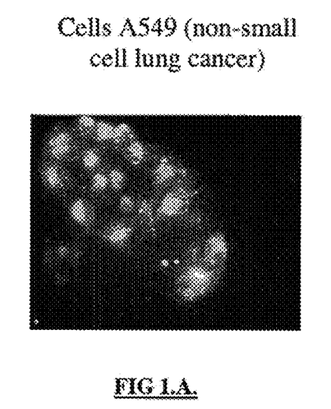

Results:

Appended FIG. 1 gives the images obtained with a standard fluorescence microscope of slide cultured cells. It shows much greater incorporation of the probe of example 1 in the tumoral cells (FIG. 1A) than in the cells from healthy tissue (FIG. 1B). This differential was also confirmed by flow cytometry.

This result confirms the advantage of using the compounds of the present invention as fluorescent diagnostic probes enabling the selection of tumors eligible for treatment with an anticancer compound vectored by the polyamine transporter.

2. Predictability of the Response to Anticancer Agents Vectored Towards the Polyamine Transport System.

To compare the incorporation of the probes such as descried above and thereby to demonstrate the predictive nature of the response to agents vectored towards the polyamine transport system, cytotoxicity was measured using a standard method (here measurement of residual ATP using the ATPlite kit from Perkin-Elmer). An anticancer compound is used, a derivative of epipodophyllotoxin, whose intracellular penetration is dependent on the polyamine transporter, such as the compound described in example 27 of patent application WO 2005/100363 and, as reference compound, etoposide which is a non-vectored epipodophyllotoxin. These two compounds have the same mechanism of action on cancer cells: they are both inhibitors of topoisomerase 2.

A panel of leukemic lines was assayed to ascertain probe incorporation, here the one described in example 1, regarding the sensitivity to a vectored agent such as the compound in example 27 of patent application WO 2005/100363 and by comparison with non-vectored etoposide. After an incubation time of 72 hours with the compound of example 27 in patent application WO 2005/100363 or with etoposide, cytotoxicity was evaluated using the ATPlite kit. Cells from the same line were also incubated in the presence of the probe described in example 1, and were analyzed by flow cytometry. Fluorescence intensity measured at 525 nm was followed from 0 to 1 hour 30 minutes and the slope of intensity variation was calculated.

Results:

Initially, the comparison of the cytotoxicity of the compound in example 27 of patent application WO 2005/100363 with etoposide having a similar mode of action, by determining a $IC_{50}$ ratio, enabled identification of the leukaemias for which vectoring held a predominant role in the efficacy of the compound.

For all the assayed lines, the capacity to incorporate the fluorescent probe, characterized by the fluorescence measured by flow cytometry, was also measured.

These results are given in Table 1 below:

TABLE 1

| Cell line | Cytotoxicity of Etoposide $IC_{50}$ (µM) | Cytotoxicity of the compound in example 27 of WO 2005/100363 $IC_{50}$ (µM) | $IC_{50}$ ratio Etoposide/ compound in example 27 of WO 2005/100363 | Polyamine* transport activity |
|---|---|---|---|---|
| CEM | 0.06 | 0.003 | 20 | 421 |
| BL-41 | 0.4 | 0.009 | 44 | 164 |
| BLUE-1 | 1 | 0.1 | 10 | 58 |
| U-937 | 0.4 | 0.04 | 10 | 33 |
| KG-1 | 5 | 5 | 1 | 17 |

*Arbitrary Unit of fluorescence: (cell intensity with probe presence) - (cell intensity without probe presence).

It is clearly apparent that fluorescence intensity is greater in the cells for which vectoring is also important.

To conclude, by measuring probe incorporation it is possible to predict better efficacy and better anti-tumor selectivity of an anticancer compound such as the compound in example 27 of patent application WO 2005/100363. These results shows that follow-up of probe incorporation allows identification of the leukemic cells having highly active polyamine transport, and hence able to be treated with efficacy by anticancer compounds vectored by the polyamine transporter.

The differential obtained by flow cytometry is comparable with that seen at histochemistry. It is possible to conduct a simpler assay by only measuring fluorescence at a given time. This was verified by performing this fluorescence measurement after an incubation time of only 1 hour and 30 minutes. This may be of advantage in a hospital environment to provide a rapid result for the selection of responding cells.

By extension, said measurements may be applied to patient blood blasts taken by blood sampling or lumbar puncture during routine analysis. Measurement of fluorescence intensity can be made using routine flow cytometry or histocytochemistry in all hospitals equipped with a cytology and/or anatomopathology unit.

The invention claimed is:

1. A method for detecting tumours expressing the polyamine transport system which comprises detecting said tumours with a diagnostic fluorescent probe a compound of general formula 1:

Formula 1 or a pharmaceutically acceptable salt thereof,
in which:
$R_1$ represents one or two $NO_2$ groups at position 4 and/or 6;
the polyamine chain can be at position 5, 6 or 7;
$R_2$ represents a hydrogen, a $C_{1-6}$alkyl, a benzyl, or a perfluoroalkyl group;
the values of a, b, and c can be 2 to 5, independently of each other, and represent alkylene chains separating the amino groups;

the values of d and e may be 0 or 1 independently, but cannot represent value 0 at the same time.

2. The method according to claim 1, wherein $R_1$=4-$NO_2$.

3. The method according to claim 1, wherein $R_1$=4-$NO_2$, $R_2$=$C_{1-6}$alkyl, a=3, b=4, c=3, and d=e=1.

4. The method according to claim 1, wherein $R_1$=4-$NO_2$, $R_2$=H or $C_{1-6}$alkyl, a=0, b=4, c=3, d=0, and e=1.

5. The method according to claim 1, wherein $R_1$=4-$NO_2$, $R_2$=H or $C_{1-6}$alkyl, a=0, b=3, c=4, d=0, and e=1.

6. The method according to claim 1, wherein $R_1$=4-$NO_2$, $R_2$=$C_{1-6}$alkyl, a=4, b=0, c=0, d=1, and e=0.

7. The method according to claim 1, wherein the compound of formula (I) is N-(3-aminopropyl)-N'-{3-[methyl-(7-nitrobenzo[1,2,5]oxadiazol-4-yl)-amino]-propyl}-butane-1,4-diamine.

8. The method according to claim 1, wherein the compound of formula (I) is N-(3-aminopropyl)-N '-methyl-N '-(7-nitrobenzo [1,2,5]oxadiazol-4-yl)-butane-1,4-diamine.

9. The method according to claim 1, wherein the compound of formula (I) is N-(3-aminopropyl)-N'-(7-nitrobenzo[1,2,5]oxadiazol-4-yl)-butane-1,4-diamine.

10. The method according to claim 1, wherein the compound of formula (I) is N*1*-{3-[methyl-(7-nitrobenzo[1,2,5]oxadiazol-4-yl)-amino]-propyl}-butane-1,4-diamine.

11. The method according to claim 1, wherein the compound of formula (I) is N*1*-[3-(7-nitrobenzo[1,2,5]oxadiazol-4-yl-amino)-propyl]-butane-1,4 -diamine.

12. The method according to claim 1, wherein the compound of formula (I) is N*1*-methyl-N*1*(7-nitrobenzo[1,2,5]oxadiazol-1,4-4-yl)butane-1,4-diamine.

* * * * *

UNITED STATES PATENT AND TRADEMARK OFFICE
CERTIFICATE OF CORRECTION

PATENT NO. : 8,569,011 B2  
APPLICATION NO. : 13/493556  
DATED : October 29, 2013  
INVENTOR(S) : Jean-Philippe Annereau et al.

Page 1 of 1

It is certified that error appears in the above-identified patent and that said Letters Patent is hereby corrected as shown below:

IN THE SPECIFICATION:

Column 1, delete lines 7-11 in their entirety, i.e., delete "NOVEL FLUORESCENT ... CANCEROUS TUMORS".

Column 1, line 20, change "Ser. No. 0,756,743" to --Ser. No. 0756743--.

Column 5, line 8, change "$R_2$=H or $C_{1-5}$ alkyl" to --$R_2$=H or $C_{1-6}$ alkyl--.

Column 7, line 5, change "$R_2$=4-$NO_2$," to --$R_1$=4-$NO_2$,--.

Column 10, line 41, change "TLC: S102" to --TLC: SiO2--.

Column 10, line 44, change "6.17 (d, 1H, J=8 Hz, $H_5$)," to --6.17 (d, 1H, J=8 Hz, $H_6$),--.

Column 10, line 61, change "3.33 (s, 3H, $NCH_2$)," to --3.33 (s, 3H, $NCH_3$),--.

Column 11, line 55, change "(d, 1H, J=8 Hz, $H_5$)," to --(d, 1H, J=8 Hz, $H_6$),--.

Column 12, line 1, change "6.44 (d, 1H, J=8 Hz, $H_5$)," to --6.44 (d, 1H, J=8 Hz, $H_6$),--.

Column 12, lines 31-32, change "6.30 (d, 1H, J=8 Hz, $H_5$)," to --6.30 (d, 1H, J=8 Hz, $H_6$),--.

IN THE CLAIMS:

Claim 12, at column 15, line 30, change "2,5]oxadiazol-1,4-4-yl)butane-1,4-diamine" to --2,5]oxadiazol-4-yl)butane-1,4-diamine--.

Signed and Sealed this  
Second Day of December, 2014

Michelle K. Lee  
*Deputy Director of the United States Patent and Trademark Office*